United States Patent
Satake et al.

[11] Patent Number: 5,801,807
[45] Date of Patent: Sep. 1, 1998

[54] OPHTHALMIC ILLUMINATION DEVICE HAVING ADJUSTABLE TRANSMITTANCE MEMBER AND MICROSCOPE FOR OPERATION USING THE SAME

[75] Inventors: Eiji Satake; Masanobu Kaneko; Ken Tomioka, all of Yokohama, Japan

[73] Assignee: Nikon Corporation, Tokyo, Japan

[21] Appl. No.: 693,402

[22] Filed: Aug. 7, 1996

[30] Foreign Application Priority Data

Aug. 8, 1995 [JP] Japan ................................. 7-222676
Sep. 28, 1995 [JP] Japan ................................. 7-251204
Dec. 22, 1995 [JP] Japan ................................. 7-335186

[51] Int. Cl.$^6$ ........................................... A61B 3/10
[52] U.S. Cl. ............................ 351/221; 351/214
[58] Field of Search ........................ 351/205, 209, 351/210, 211, 213, 221, 214

[56] References Cited

U.S. PATENT DOCUMENTS 5,512,965  4/1996  Snook .................... 351/205
5,555,040  9/1996  Kaneko ................. 351/221

FOREIGN PATENT DOCUMENTS 60-111625  6/1985  Japan.
07-148179  6/1995  Japan.

Primary Examiner—Huy Mai
Attorney, Agent, or Firm—Shapiro and Shapiro

[57] ABSTRACT

This invention provides a microscope for operation which can form a black point for protecting a patient's retina even when the retina part is not at the center of the field of view of the microscope. The microscope for operation has an X-Y stage for moving the microscope body, a CCD camera for obtaining an image in the field of view of the microscope, a liquid crystal device provided with a light transmitting surface transmitting illuminating light therethrough and comprised of display dots disposed in the form of a matrix, and a control device for controlling and driving the liquid crystal device. The control device analyzes the image in the field of view of the microscope obtained by the CCD camera to thereby recognize the position of the retina part of an eye to be examined, and the display dots positioned in that area on the light transmitting surface of the liquid crystal device which has been determined correspondingly to the recognized position are selectively colored to thereby constitute a black point filter.

16 Claims, 14 Drawing Sheets

OPHTHALMIC ILLUMINATION DEVICE HAVING ADJUSTABLE TRANSMITTANCE MEMBER AND MICROSCOPE FOR OPERATION USING THE SAME

BACKGROUND OF THE INVENTION

1. Field of the Invention

This invention relates to an ophthalmic illumination device, and particularly to a device for protecting the tissue of an eye from excessive illuminating light in the illuminating optical system of a microscope for operation.

2. Related Background Art

In recent years, as typified by the operation on cataract, operations using a microscope have been widely practiced. However, the illuminating light of a microscope for operation is very great in its intensity and the time required for an operation is relatively long. Therefore, the tissue of the fundus part of an eye to be examined may be injured by rays of illuminating light entering, for example, from the pupil of the eye to be examined.

There have heretofore been made various propositions for protecting the tissue of an eye from excessive illuminating light in a microscope for operation.

For example, Japanese Patent Application Laid-Open No. 60-111625 discloses a technique of disposing a light absorbing layer in a plane conjugate with an object surface in an illuminating optical path, and inserting this light absorbing layer into the optical path of an illuminating optical system as required.

However, in the prior art disclosed in the above-mentioned publication, all of illuminating light is intercepted by the insertion of the light absorbing layer. This has led to the inconvenience that even in a case where more or less brightness is necessary in a region to be treated, for example, as in a suturing process, the region to be treated becomes too dark by the insertion of the light absorbing layer and an operation becomes difficult to perform. Also, even when the intensity of the illuminating light is relatively small and the intensity of the illuminating light in the central portion corresponding to the pupil of an eye to be examined can be made great, there has been no other countermeasure than to retract the light absorbing layer from the illuminating optical path. Further, the light absorbing layer which is a light intercepting member must be mechanically inserted or retracted, and this has led to the inconvenience that vibration occurs each time the light intercepting operation is performed and as a result, the vibration is also transmitted to the microscope.

As another microscope for operation according to the prior art, there is one which will be described below. In an operation for mounting an IOL (intraocular lens) on a catract patient, if illuminating light is directly applied to the patient's retina when the crystalline lens is removed and the IOL is inserted, the patient's retina may be damaged. Therefore, the microscope for operation according to the prior art has been provided with a so-called black point filter which is glass or the like having a circular black point printed thereon and adapted to be inserted into or retracted from an illuminating optical path as required to thereby protect a patient's retina. As a microscope for operation according to the prior art, there is one disclosed, for example, in Japanese Patent Application Laid-Open No. 7-148179. The construction of this microscope for ophthalmic operation according to the prior art will hereinafter be described with reference to FIG. 24 of the accompanying drawings.

In FIG. 24, the reference numeral 1001 designates an eye to be examined, and the reference numeral 1002 denotes an operator's eye. The observation image of the eye 1001 to be examined passes through a half mirror 1030, a first objective lens 1011 and a pair of right and left variable power optical systems 1012 (in the figure, only one optical path is shown). The observation image of the eye 1001 to be examined having passed through the variable power optical systems 1012 passes through a second objective lens 1031, an erect prism 1032 and a lozenge-shaped prism 1033, and is imaged on the operator's eye 1002 by an eyepiece 1034.

Illuminating light to the eye 1001 to be examined is produced by a light source 1025 electrically controlled by an illuminating power source 1040, passes through an illuminating optical system 1020 comprising a condenser lens 1022 and a relay lens 1021, through the intermediary of an optical fiber 1026, and is deflected to the eye 1001 to be examined by a half mirror 1030.

In the optical path of the illuminating optical system 1020, an eye fixation target 1023 is installed at a position conjugate with the retina 1001b of the eye 1001 to be examined. The eye fixation target 1023 is mechanically pivotally movably supported so as to be freely manually moved in a plane (XY direction) orthogonal to the optical axis to turn the eye 1001 to be examined in any direction.

As a mechanism for moving the eye fixation target 1023, use is made of an eye fixation target moving mechanism 1030 which, as shown, for example, in FIG. 25 of the accompanying drawings, is provided with an operating rod 1301 having the eye fixation target 1023 secured to the tip end portion thereof and formed with an operating portion 1303 on the opposite side thereof, and a supporting portion for pivotally supporting the operating rod 1301.

In the prior art as described above, the eye fixation target 1023 is placed at the position conjugate with the retina 1001b and it is possible for the eye 1001 to be examined to recognize the shape thereof. But the shape of the eye fixation target 1023 is physically fixed and in many cases, a black point having a simple shape is used as the eye fixation target. Therefore, the best use is not made of the point that the eye fixation target 1023 is disposed at the position conjugate with the retina 1001b, of the ability of the eye 1001 to be examined to recognize the shape of the eye fixation target.

Also, this black point is usually designed to lie at the center of the field of view of the microscope. However, the retina part does not always lie at the center of the field of view during an operation, but the retina part and the position of the black point may sometimes deviate from each other. This is because the operator operates an X-Y stage to thereby move the microscope body and it often takes place to install the optimum place at the center of the field of view in each process of the operation. As a result, the black point filter according to the prior art has suffered from the problem that when a patient's retina does not lie at the center of the field of view, the formed black point does not cover the retina and the function as retina protection does not sufficiently work.

SUMMARY OF THE INVENTION

It is an object of the present invention to provide a microscope for operation provided with a light transmitting element capable of applying an optical pattern for an ophthalmic operation in an improved maner to an eye to be examined and having a light transmitting surface that has a variable transmission factor in a predetermined area.

It is also an object of the present invention to provide an ophthalmic illumination device capable of forming a black point for protecting a patient's retina even when the retina part does not lie at the center of the field of view of a microscope.

It is a further object of the present invention to provide an ophthalmic illumination device provided with fixation target forming means capable of more easily forming various recongnizable fixation targets for an eye to be examined, at a position conjugate with the retina portion of the eye to be examined.

To solve the above-noted problems, according to the present invention, there is provided an ophthalmic illumination device provided with an illuminating optical system for illuminating an eye to be examined, a light transmitting member disposed in the optical path of the illuminating optical system and having a light transmitting surface variable in the transmission factor for illuminating light, and a control unit for varying the transmission factor of a predetermined area of the light transmitting surface of the light transmitting member.

The light intercepting operation while illuminating light to the eye to be examined is performed by electrically varying the transmission factor and therefore, unlike the insertion and retraction of a mechanical light intercepting member, no vibration occurs during the light intercepting operation. Accordingly, for example, no vibration is transmitted to the microscope for operation and therefore, the eye to be examined becomes easy to observe. Also, even when the patient's retina part does not lie at the center of the field of view of the microscope, the retina part can be protected.

According to a preferred embodiment, the light transmitting member has a circular central area corresponding to the pupil of the eye to be examined, and a marginal area surrounding the central area, and the control portion may preferably vary the light transmission factor of the central area and the marginal area independently of each other.

Thus, the transmission factor of the central light intercepting portion and the transmission factor of the marginal light intercepting portion can be suitably varied to thereby realize various light intercepting states. That is, the eye to be examined can be illuminated in such a suitable light intercepting state that the tissue of the fundus portion of the eye to be examined is not injured. Also, in an operation on cataract, it becomes possible to protect the fundus part of the eye to be examined from excessive illuminating light and at the same time, an operation comfortable to an operator becomes possible.

Further, it is preferable that the light transmitting member be provided at a position optically conjugate with the retina part of the eye to be examined, and the control portion vary the transmission factor of a predetermined area of the light transmitting surface of the light transmitting member and form a fixation target to be recognized by an examine.

Thus, an operator can present a predetermined fixation target to an eye to be operated during an operation and therefore can practice various visual examinations more easily.

DESCRIPTION OF THE PREFERRED EMBODIMENTS

A first embodiment of a microscope for operation to which an ophthalmic illumination device is applied will hereinafter be described with reference to the drawings.

Figure 1:
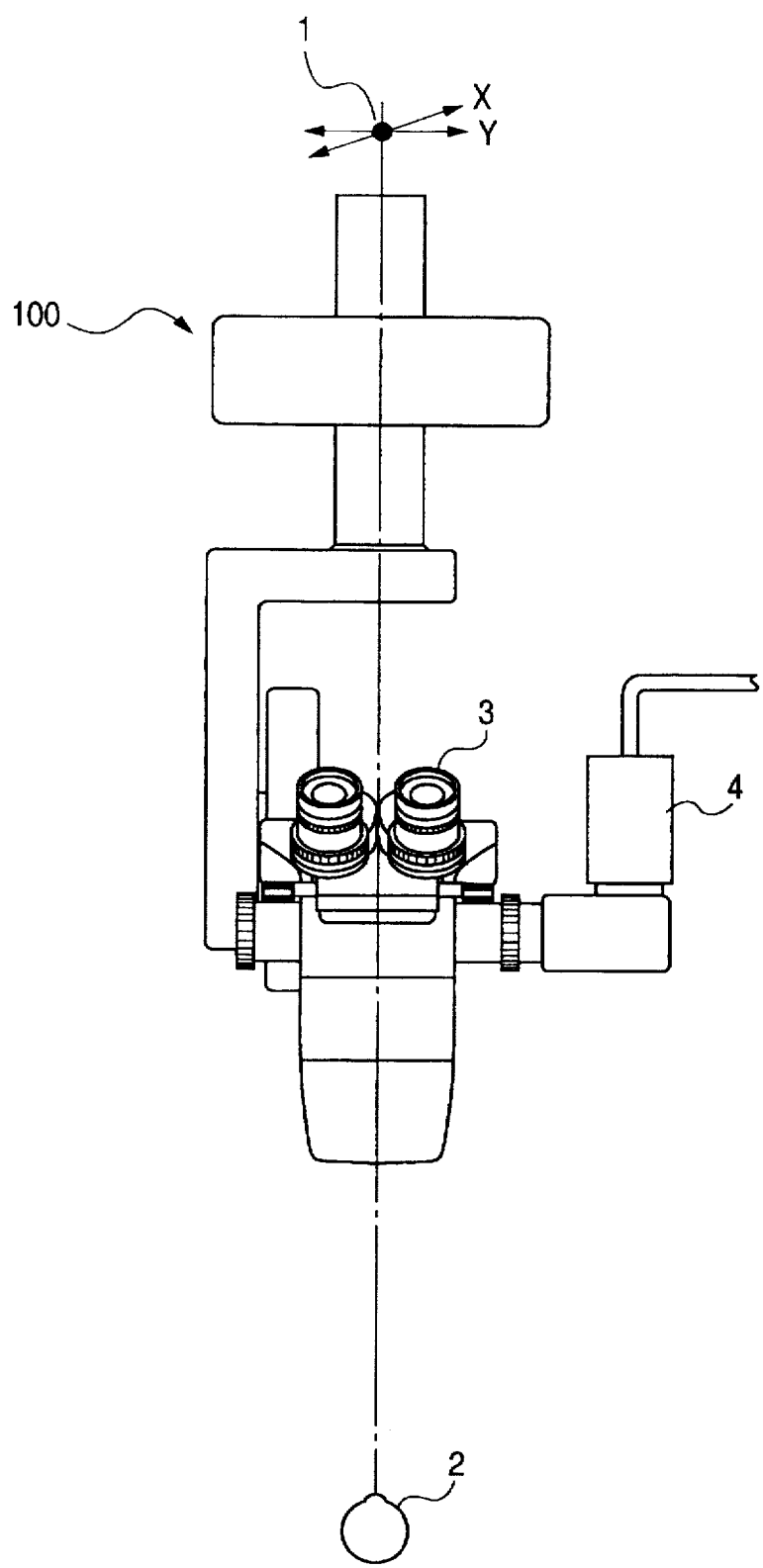
FIG. 1 is an illustration schematically showing a microscope for operation according to the present invention.

As shown in the pictorial view of FIG. 1, the microscope for operation is provided with a microscope body 100 and an X-Y stage 1 for moving the microscope body 100 in X and Y directions. The microscope body 100 is provided with an eyepiece unit 3, a CCD camera 4 for obtaining the field image of the microscope, an observation optical system for observing an eye 2 to be examined and an illuminating optical system for illuminating the eye 2 to be examined. The X-Y stage 1 is provided with an X-axis motor and a Y-axis motor for moving the microscope body 100 in X and Y directions, respectively, and can be driven to a desired position by an operating switch for controlling the operation of each motor.

In case of the use of the microscope for operation, an operator moves the X-Y stage 1 so that a particular region in the eye 2 to be examined may enter the field of view of the microscope, while looking into the eyepiece unit 3.

Figure 2:
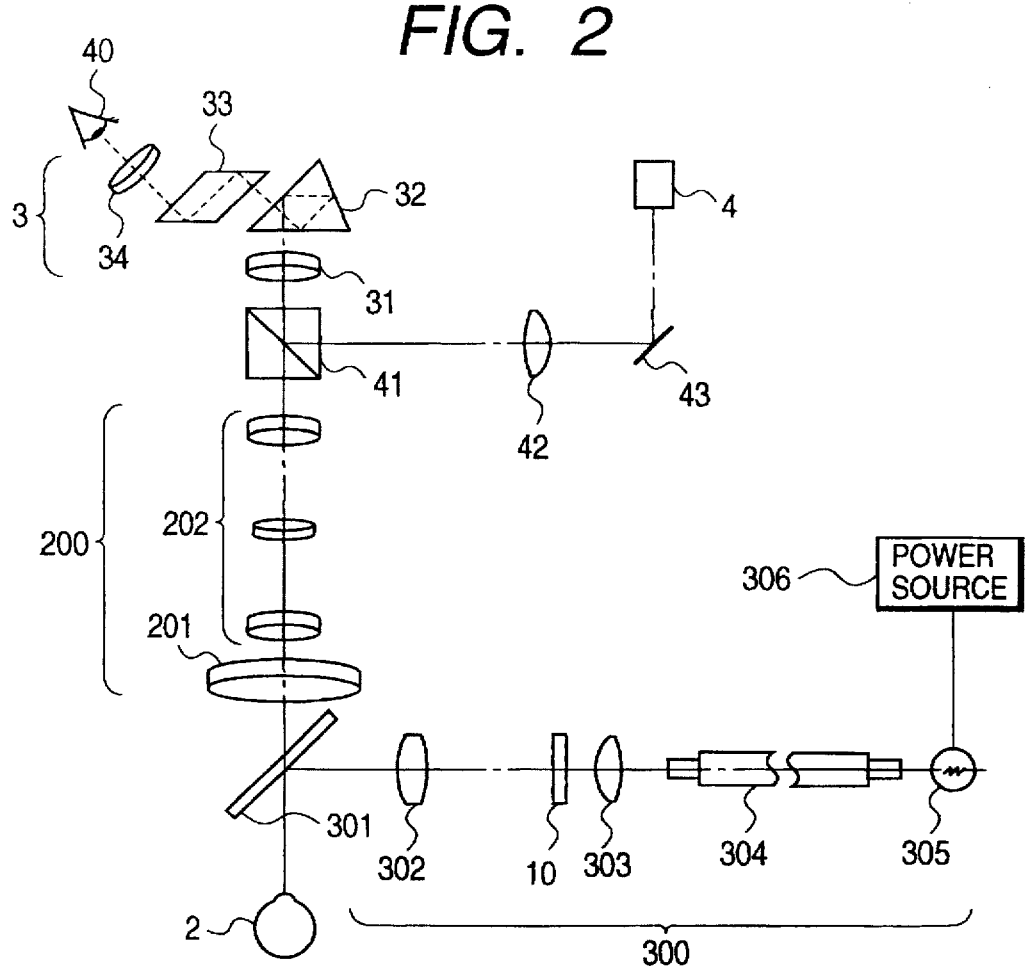
FIG. 2 shows an example of the construction of an optical system according to a first embodiment.

An example of the construction of an optical system according to a first embodiment will now be described with reference to FIG. 2.

The eyepiece unit 3 has an imaging lens 31, an erect prism 32, a lozenge-shaped prism 33 and an eyepiece 34. The observation optical system 200 has an objective lens 201, and a pair of zoom lens systems 202 (only one of which is shown) for stereoscopically viewing the eye 2 to be examined. The reference numeral 40 designates the operator's eye.

The illuminating optical system 300 has an illumination power source 306, an illuminating lamp 305 such as a halogen lamp supplied with electric power from the illumination power source 306, an optical fiber 304 for sending the illuminating light from the illuminating lamp 305, a condenser lens 303 a relay lens 302 and a half mirror 301 for directing the illuminating light from the optical fiber 304 to the eye 2 to be examined.

The optical system according to the present embodiment is further provided with a liquid crystal device (light transmitting element) 10 of the transmission type disposed in the illuminating optical path between the condenser lens 303 and relay lens 302 of the illuminating optical system 300. This liquid crystal device 10 is one of the features of the construction of the present invention, and is provided with a light transmitting surface capable of varying the transmission factor of any area. Therefore, the transmission factor of a predetermined area of the light transmitting surface of the liquid crystal device 10 can be varied to thereby vary the light intensity in that area in the illuminated area illuminated by the illuminating light passing through the light transmitting surface which corresponds to said predetermined area.

In the present embodiment, description will be made of a case where an area is designated in the light transmitting surface of the liquid crystal device 10 in which the transmission factor is varied so that a black point for the protection of the retina of the eye to be examined may be formed in the illuminating light. Of course, it is also possible to change the position and shape of the area in which the transmission factor of the liquid crystal device 10 is varied, to thereby form not only the black point but any optical pattern and apply it onto the eye to be examined.

Figure 3:
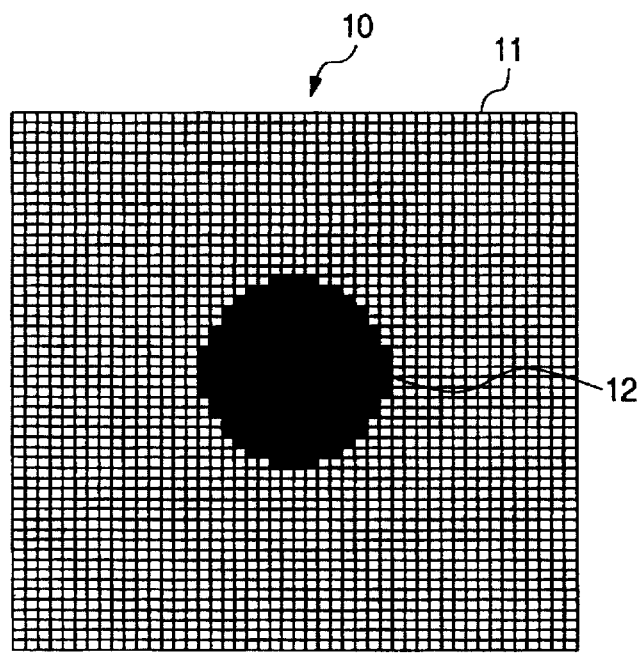
FIG. 3 is an illustration showing an example in which a black point filter directed to retina protection is constructed by a liquid crystal device of a dot matrix type.

As the liquid crystal device 10, use is made of one as shown, for example, in FIG. 3 wherein display dots of a predetermined size are arranged in the form of a matrix and constitute a light transmitting surface 11. When the liquid crystal device 10 of such a dot matrix shape is used as a black point filter for the protection of the retina of the eye to be examined, the necessary display dots in the light transmitting surface 11 are colored (reduced in transmission factor) so that a circular area 12 corresponding to the black point is formed. The control of this liquid crystal device 10 will be described later.

While the liquid crystal device 10 is used in the present embodiment, the light transmitting element of the present invention is not restricted to the liquid crystal device, but use may be made of any other optical element such as an electrochromic element which can form light and shade in a pre-designated area in the illuminating light.

The optical system according to the present embodiment further has, as an optical system for directing the field image of the microscope to the CCD camera 4, a beam splitter 41 disposed between the imaging lens 31 and the observation optical system 200, and a projection lens 42 and a mirror 43 for directing the light divided by the beam splitter 41 to the CCD camera 4.

Figure 4:
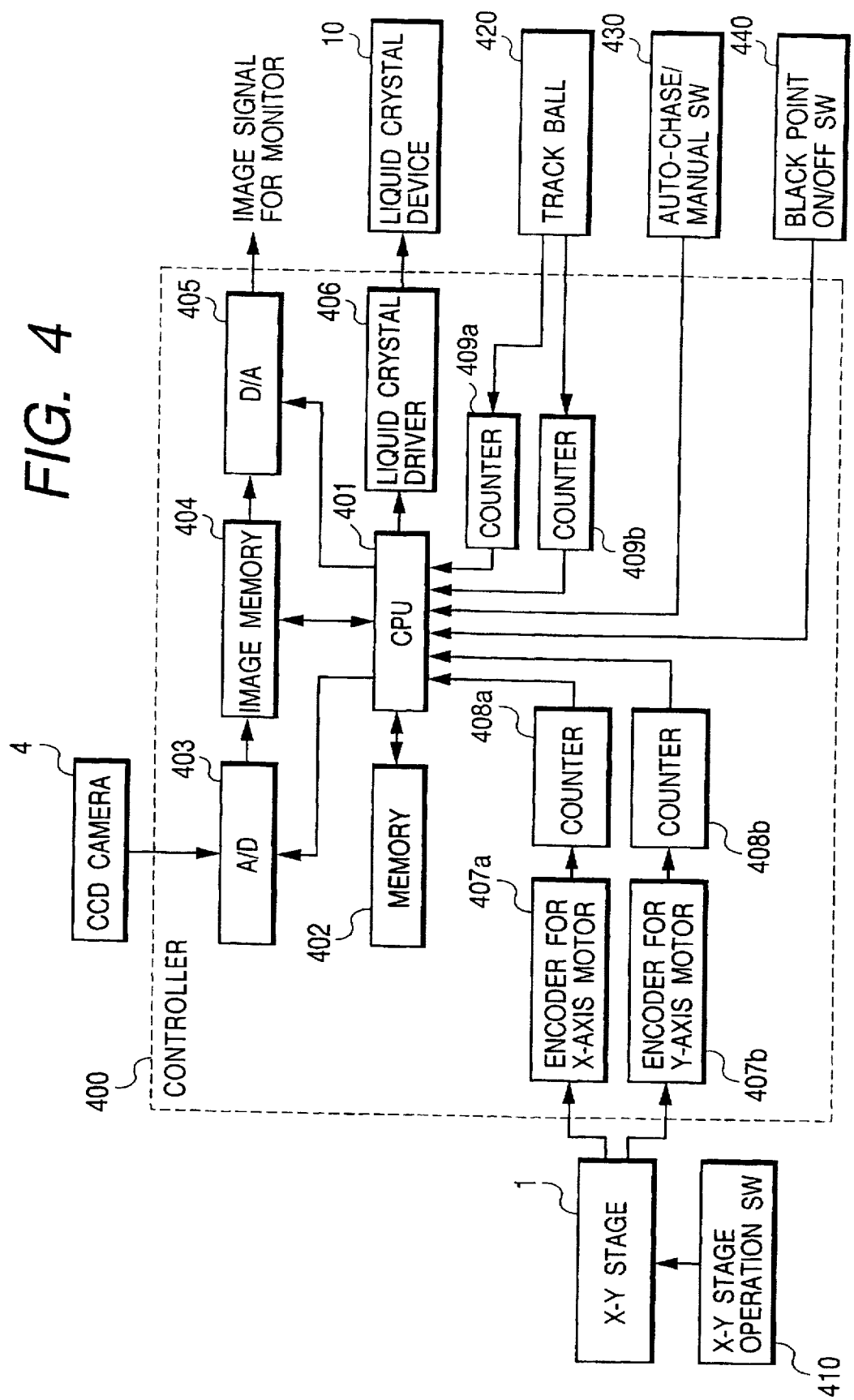
FIG. 4 is a black diagram showing an example of the circuit construction of the first embodiment.

An example of the circuit construction of the present embodiment will now be described with reference to FIG. 4.

The device of the present embodiment has a control device 400 for receiving data from the CCD camera 4, the X-Y stage 1, etc. and effecting the control of the liquid crystal device 10, an X-Y stage operation switch 410 for receiving an operation regarding the designation of the amount of movement of the X-Y stage 1, and a track ball 420 for receiving a manual operation for moving the position of a formed black point. While the track ball 420 is used in the present embodiment, for example, a joy stick or the like capable of inputting any amount of operation may be used as an inputting device.

The device of the present embodiment further has an auto-chase/manual changeover switch 430 for effecting the changeover of automatically (auto) moving the position of the black point or moving it by a manual operation, and a black point ON/OFF switch 440 controlling whether the black point should be formed.

The control device 400 has a memory 402 storing therein various programs for setting a control method or the like for the liquid crystal device 10, a CPU 401 for executing the programs stored in the memory 402 to thereby effect the control of the liquid crystal device 10, and a liquid crystal driver 406 for driving the liquid crystal device 10 in conformity with the control by the CPU 401.

The control device 400 further has an A/D converter 403 for receiving the image signal of the eye 2 to be examined and the margin thereof from the CCD camera 4 and digitally converting it, an image memory 404 for temporarily storing the digitized image data therein, and a D/A converter 405 for analogously converting the image data stored in the image memory 404 and image data indicative of the position or area of the black point set by the CPU 401, and outputting it as an image signal to a monitor display (not shown).

The monitor display receives the image signal from the D/A converter 405 and displays the image in the field of view of the microscope. During initial setting of the black point or while the black point is turned off, an object or target which indicates the position or area at which the black point is to be formed is superposingly displayed over the image in the field of view of the microscope on the monitor display.

The CPU 401 executes well-known image processing such as binarization at a predetermined period by the use of the image data stored in the image memory 404 to thereby sequentially detect at what position in the field of view of the microscope the center of the pupil, i.e., the retina part of the eye 2 to be examined, lies. The CPU 401 further specifies an area corresponding to the detected position of the retina part of the eye 2 to be examined on the light transmitting surface 11 of the liquid crystal device 10, and reduces the transmission factor of the display dot of the liquid crystal device 10 positioned in the specified area so as to form a black point for retina protection (see FIG. 3).

The control device 400 further has a counter 409a for counting the amount of operation of the track ball 420 in the X direction in predetermined units, a counter 409b for counting the amount of operation of the track ball 420 in the Y direction in predetermined units, an X-axis motor encoder 407a and a Y-axis motor encoder 407b for detecting the amounts of rotation of the X-axis motor and Y-axis motor corresponding to the amount of movement of the X-Y stage 1, and counters 408a and 408b for counting the amounts of rotation detected by the two encoders in predetermined units.

In the present embodiment, whether the operation of specifying the position of the retina part should be automatically performed or manually performed is changed over by the auto-chase (or homing)/manual changeover switch 430. When the manual operation has been selected by the auto-chase/manual changeover switch 430, the CPU 401 reads a signal corresponding to the amount of operation of the track ball 420 through the counter 409, and the CPU 401 controls the liquid crystal driver 406 in conformity with the amount of operation of the track ball 420, and displaces the area in which the transmission factor of the liquid crystal device 10 is reduced, in X and Y directions to thereby move the black point.

When the auto-chase has been selected, as described above, for example, an image analyzing process using the image data obtained by the CCD camera 4 is carried out, whereby the CPU sequentially specifies the position of the retina part of the eye 2 to be examined, and forms a black point in an area corresponding to that position.

Also, design may be made such that when the auto-chase has been selected, instead of the above-described image analyzing process, the black point is moved in conformity with the amount of movement of the X-Y stage 1. That is, the central position and area of the black point are set by a predetermined initial setting process, and subsequently, the CPU 401 reads a signal indicative of the amount of movement of the X-Y stage 1 through the counters 408a and 408b. Further, the CPU 401 controls the liquid crystal driver 406 in conformity with the amounts of movement in X and Y directions by the X-Y stage 1 and displaces the area in which the transmission factor of the liquid crystal device 10 is reduced which corresponds to the black point in X and Y directions to thereby move the black point.

As the predetermined initial setting process, for example, the manual operation mode is set at first, and the designation about the central position of the retina part of the eye 2 to be examined is received by the operation of the track ball 420 by the operator. Subsequently, the operator's designation regarding the size of the circular black point centering around the central position designated in this manner is received through the track ball 420. Finally, the designated central position and size are set as the central position and size of the black point.

An example of the controlling operation for the liquid crystal device 10 in the present embodiment will now be described with reference to the flow charts of FIGS. 5 and 6.

An example of the operation when the image analyzing process is used when the chase mode of the black point for the retina part is set to auto will first be described with reference to FIG. 5.

In this example of the operation, at a step 501, whether the chase is auto or manual is judged from the setting of the auto-chase/manual changeover switch 430. When auto is selected, advance is made to a step 502, where by the use of the image data in the field of view of the microscope introduced by the CCD camera 4, the position and size of the retina part of the eye 2 to be examined are determined, for example, by the image analyzing process as described above. At the step 502, further the area on the light transmitting surface of the liquid crystal device 10 which corresponds to said determined position and size of the retina part is determined, and a display dot positioned in this determined area is specified.

Also, design may be made such that what is determined by the image analyzing process at the step 502 is only the central position of the retina part and the shape of the black point is a circular shape of a predetermined size centering around said determined central position.

At a step 503, whether a black point should be formed is judged from the setting of the black point ON/OFF switch 440. When the black point ON is selected, advance is made to a step 504, where the transmission factor of the display dot of the display dots constituting the light transmitting surface of the liquid crystal device 10 which has been specified at the step 502 is reduced. When the black point ON is not selected, return is made to the step 501.

When at the step 501, manual is selected as the chase mode, advance is made to a step 512, where the initial setting of the position and size of the black point is effected. In the initial setting, the operator moves the track ball 420 and designates the central position of the retina part of the eye 2 to be examined at first, and then sets the size of the black point so that a circular black point having such a degree of size that the retina part is sufficiently covered may be formed with said designated central position as the center.

At a step 513, variations in the values of the counters 409a and 409b are read to thereby judge whether the track ball 420 has been operated, and when it has been operated, advance is made to a step 514, and when it has not been operated, the judging process of this step is repeated a predetermined time after.

When it is judged that the track ball 420 has been operated, at a step 514, the amount of operation of the track ball 420 is read through the counters 409a and 409b, and in conformity with the read amount of operation, the central position of the black point being set at that point of time is moved. At a step 514, further that area on the light transmitting surface of the liquid crystal device 10 which corresponds to the central position of the black point after moved is determined, and the display dot positioned in this area is specified.

At a step 515, whether a black point should be formed is judged from the setting of the black point ON/OFF switch 440. When the black point ON is selected, advance is made to a step 516, where the transmission factor of the display dot of the display dots constituting the light transmitting surface of the liquid crystal device 10 which has been specified at the step 514 is reduced. When the black point ON is not selected, return is made to the step 513.

At a step 517, whether the chase mode at that point of time is auto or manual is judged from the setting of the auto-chase/manual changeover switch 430. When auto is selected, return is made to the step 502, and when manual is selected, return is made to the step 513.

In this example of the operation, the image in the field of view of the microscope is directed to the CCD camera 4 and that image is analyzed to thereby recognize a place corresponding to the retina part of the eye 2 to be examined, and in accordance therewith, a display dot of the matrix-like liquid crystal device 10 which is to be colored is selected to thereby constitute a black point filter.

According to this example of the operation, the position of the retina part of the eye 2 to be examined is always grasped by the image analyzing process of the field image of the microscope and therefore, even if the X-Y stage 1 is operated to move the field of view of the microscope, the display dot of the liquid crystal device 10 which is to be colored in conformity therewith can be automatically changed. Therefore, it becomes possible to realize a black point filter which always function as patient's retina protecting means.

An example of the operation in which when the chase mode is auto, the black point is moved in conformity with the amount of movement of the X-Y stage 1 will now be described with reference to the flow chart of FIG. 6.

Figure 5:
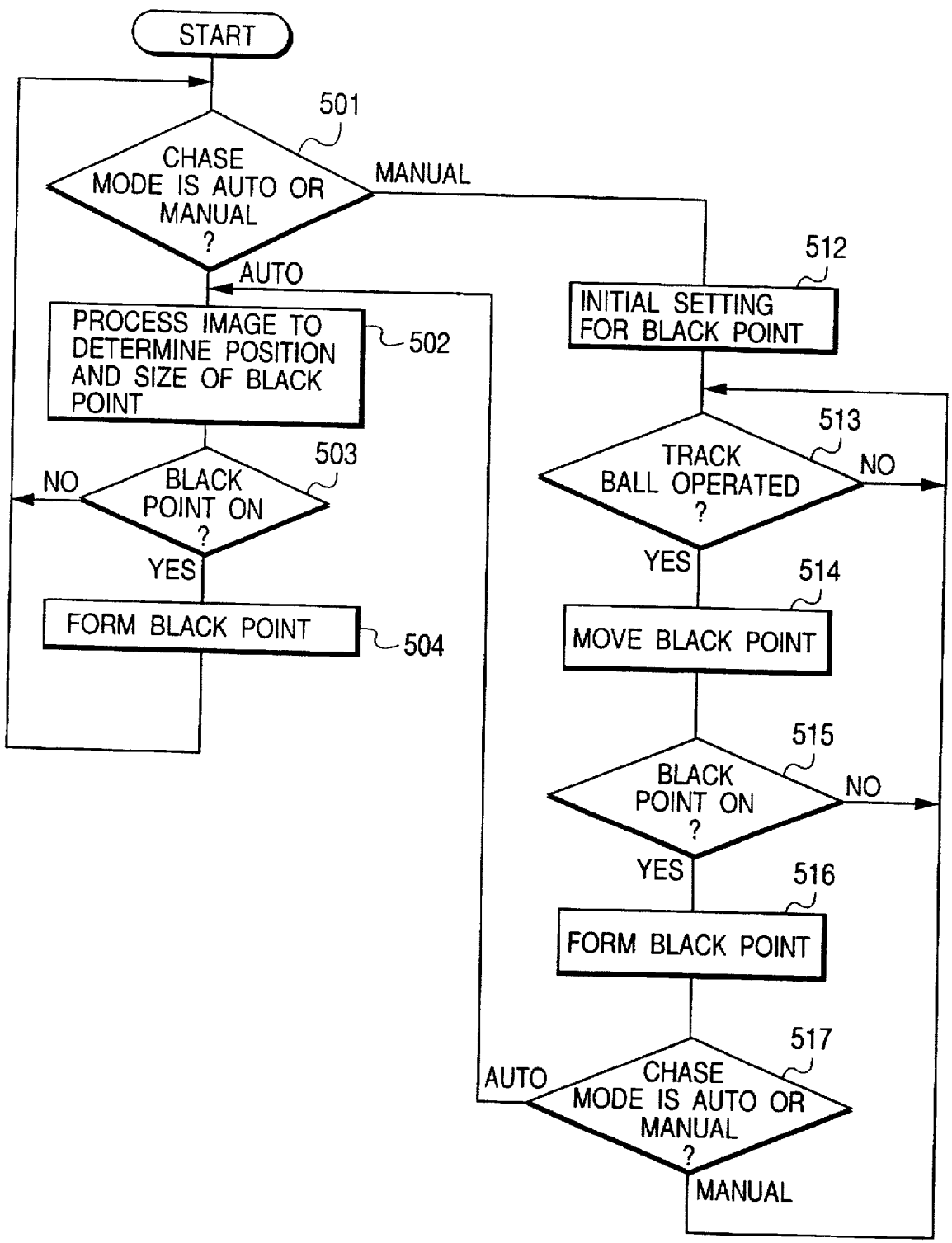
FIG. 5 is a flow chart showing an example of the control processing operation of the liquid crystal device in the first embodiment.
Figure 6:
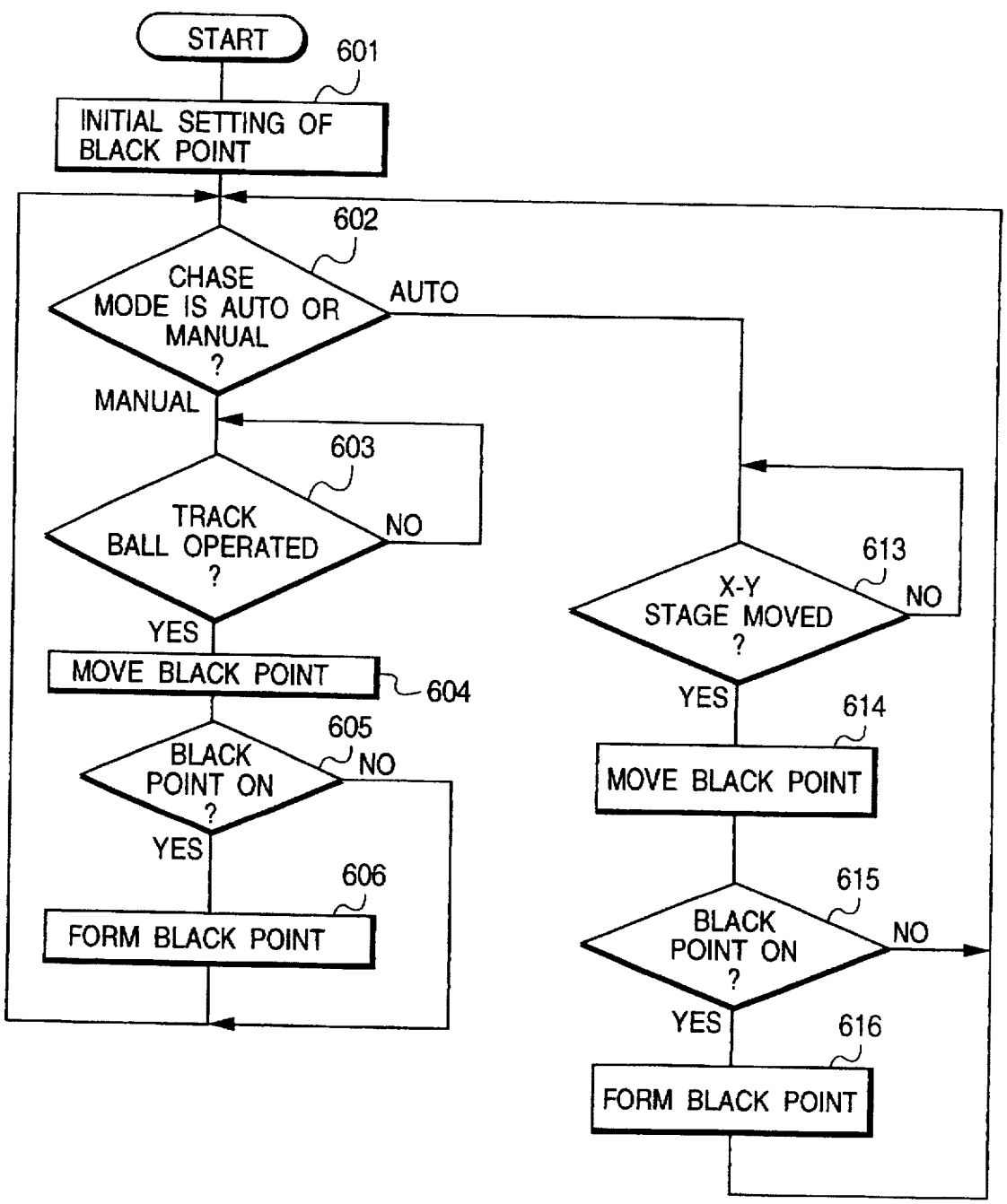
FIG. 6 is a flow chart showing another example of the control processing operation of the liquid crystal device in the first embodiment.

In this example of the operation, the initial setting process of a black point similar to the step 512 of FIG. 5 is first executed at a step 601, and at a step 602, whether the chase mode at that point of time is auto or manual is judged from the setting of the auto-chase/manual changeover switch 430. When auto is selected, advance is made to a step 613, and when manual is selected, advance is made to a step 603.

When manual is selected, steps 603 to 606 which are the same processes as the steps 513 to 516 of FIG. 5 are executed, whereby a process such as moving the position of the black point in conformity with the amount of operation of the track ball 420 is carried out, and return is made to the step 602.

When auto is selected, the count values of the counters 408a and 408b are read at the step 613, whereby whether the X-Y stage 1 has been moved is judged, and if it has not been moved, the judging process of this step is repeated a predetermined time after.

When at the step 613, it is judged that the X-Y stage has been moved, at a step 614, the amounts of movement of the X-Y stage 1 in the X-axis direction and the Y-axis direction are read through the encoders 407a, 407b and the counters 408a, 408b, and the central position of the black point set at that point of time is moved in conformity with the read amounts of movement. At the step 614, that area on the light transmitting surface of the liquid crystal device 10 which corresponds to the central position of the black point after moved is further determined, and a display dot positioned in that area is specified.

At a step 615, whether a black point should be formed is judged from the setting of the black point ON/OFF switch 440. When the black point ON is selected, advance is made to a step 616, where the transmission factor of the display dot of the display dots constituting the light transmitting surface of the liquid crystal device 10 which has been specified at the step 614 is reduced. When the black point ON is not selected, return is made to the step 602.

According to this example of the operation, even if the X-Y stage 1 is operated to thereby move the field of view of the microscope, the display dots of the liquid crystal device 10 which are to be colored in conformity with the amounts of movement of the X-Y stage can be automatically changed. Therefore, it becomes possible to realize a black point filter always functioning as patient's retina protecting means.

According to the present embodiment, as described above, even when the retina part of the eye 2 to be examined is not placed at the center in the field of view of the microscope, the black point for retina protection can cover the retina part and therefore, there is obtained the effect that the retina of the eye to be examined can always be protected.

Also, in the present embodiment, description has been made of an example in which the liquid crystal device (light transmitting element) provided in the microscope for operation is used for the formation of a black point for retina protection, but the liquid crystal device is also usable for the following uses.

For example, it can be used for the marking of a cornea incision position during IOL operation. Again in this case, as in the above-described embodiment, a particular region is recognized by the image analyzing process and an area on the light transmitting surface of the liquid crystal device 10 in which the transmission factor is reduced is designated so that an optical mark of a predetermined shape may be applied to that region. Also, design may be made such that as in the above-described embodiment, an optical mark of a predetermined shape is applied to a position selected by initial setting and the liquid crystal device 10 is controlled so that this mark may be moved in conformity with the movement of the X-Y stage 1. According to such a construction, irrespective of the movement of the field of view of the microscope, optical marking can always be effected to a particular region and therefore, it becomes possible to carry out an operation more efficiently.

Also, the area in which the transmission factor is reduced is designated so that the illuminating light may be transmitted in the form of a slit through the light transmitting surface of the liquid crystal device, whereby the liquid crystal device may be used in a manner similar to that in which a slit lamp is used. Further, design may be made such that an area of the liquid crystal device in which the transmission factor is reduced is selected so that an optical pattern may be formed in the form of a number of concentric circles, and this optical pattern is applied to the patient's cornea surface, whereby the situation of astigmatism is confirmed.

Figure 7:
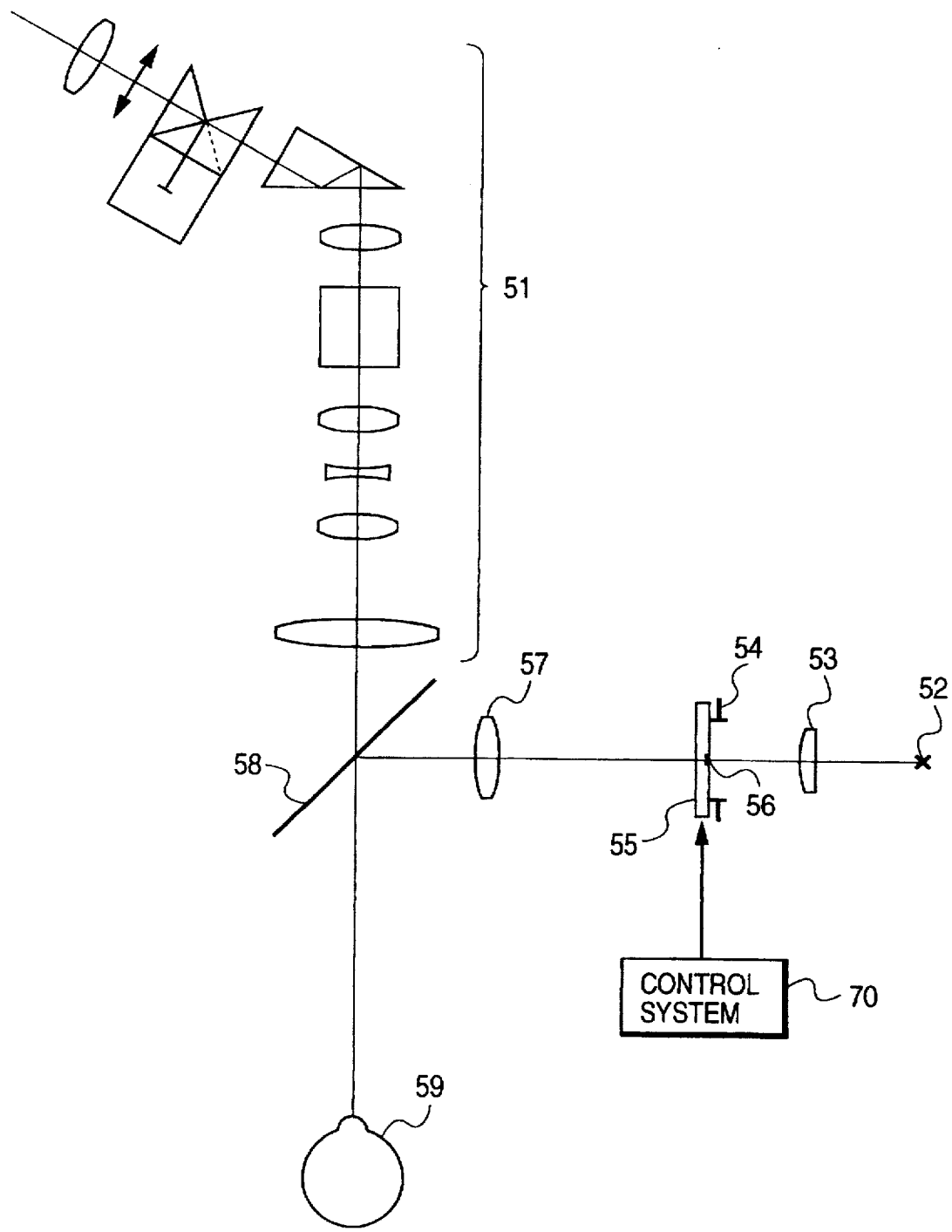
FIG. 7 shows an example of the construction of an optical system according to a second embodiment.

FIG. 7 shows the construction of an ophthalmic illumination device according to a second embodiment of the present invention together with the optical system of a microscope. In FIG. 7, the reference numeral 51 designates the optical system of a binocular stereoscopic microscope.

The ophthalmic illumination device shown is provided with an illuminating light source 52. Illuminating light emitted from the illuminating light source 52 is condensed by a condenser lens 53 and illuminates an illumination field diaphragm 54. In an illuminating optical system not provided with a light intercepting member, nothing is provided near the illumination field diaphragm 54 and therefore, the illuminating light passed through the illumination field diaphragm 54 passes through a relay lens 57 for illumination, whereafter it is reflected downwardly as viewed in FIG. 7 by light dividing means such as a half mirror and illuminates the anterior segment of an eye 59 to be examined.

The illumination field diaphragm 54 and the pupil of the eye 59 to be examined are substantially optically conjugate with each other and therefore, the eye 59 to be examined is illuminated in the shape (usually a circular shape) of the illumination field diaphragm 54.

Figure 9:
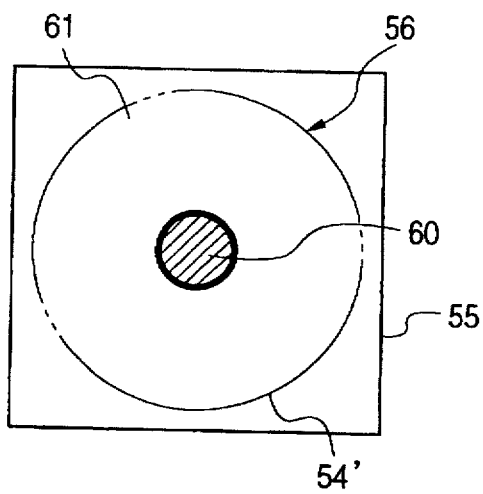
FIG. 9 shows the construction of the light intercepting member 55 of FIG. 7 along a plane perpendicular to the optical axis.

In the device according to the second embodiment, a light intercepting member 55 is provided at or near the position of the illumination field diaphragm 54. FIG. 9 shows the construction of the light intercepting member 55 along a plane perpendicular to the optical axis. As shown in FIG. 9, the light intercepting member 55 has a light intercepting portion 56 within a range 54' corresponding to the illumination field diaphragm 54. Thus, the image of the light intercepting portion 56 of the light intercepting member 55 is also formed near the anterior segment of the eye 59 to be examined.

The light intercepting portion 56, as shown in FIG. 9, has a circular central light intercepting portion 60 corresponding to the size of the pupil of the eye 59 to be examined, and a marginal light intercepting portion 61 occupying the other area within the range 54' than the central light intercepting portion 60. The central light intercepting portion 60 and the marginal light intercepting portion 61 each is formed of an electrical light control element capable of electrically varying the transmission factor. Accordingly, the transmission factor of the central light intercepting portion 60 and the transmission factor of the marginal light intercepting portion 61 can be controlled independently of each other.

Figure 8:
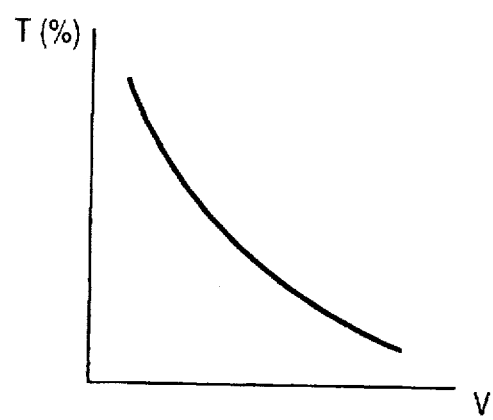
FIG. 8 is a graph showing the relation between a voltage V applied to an electrical light control element and the transmission factor T(%) thereof.

FIG. 8 is a graph showing the relation between a voltage V applied to the electrical light control elements and the transmission factor T(%) thereof. As shown in FIG. 8, in the electrical light control elements, as the voltage V applied thereto increases, the transmission factor T(%) thereof drops monotonously.

Accordingly, for example, prior to the use of the microscope, the voltage values applied to the central light intercepting portion 60 and the marginal light intercepting portion 61 are adjusted, whereby the transmission factor of each light intercepting portion can be set to a predetermined value within a range of variation. Also during the use of the microscope, it is possible to suitably vary the transmission factor of each light intercepting portion.

For example, in an operation on cataract, it is necessary to brightly illuminate the anterior segment near the crystalline lens which is a region to be operated until an intraocular lens is inserted into the eye 59 to be examined. Accordingly, until the point at which the intraocular lens is inserted, the central light intercepting portion 60 and marginal light intercepting portion 61 of the light intercepting member 55 are both rendered into a transmitting state (transparent state). Thus, the illuminating light can illuminate the eye 59 to be examined with sufficient brightness, without being intercepted by the light intercepting member 55.

At the stage of the suturing process after the point of inserting, it is desirable that the eye 59 to be examined be illuminated by the light having entered from the pupil of the eye 59 to be examined within such a range that the tissue of the fundus part of the eye is not injured while such a degree of brightness that will not hinder the suturing process is secured. Accordingly, at the point of the suturing process, as shown in FIG. 9, the transmission factor of the central light intercepting portion 60 is suitably reduced while the marginal light intercepting portion 61 is left in a transmitting state. Thus, the illuminating light to the pupil of the eye 59 to be examined is intercepted to a certain degree and at the same time, the margin of the pupil is illuminated brightly. That is, the eye 59 to be examined can be illuminated with a degree of brightness which is sufficient for the suturing process and does not injure the tissue of the fundus part of the eye.

The operation of varying the transmission factor of the central light intercepting portion 60 and the marginal light intercepting portion 61 is electrically performed through a control system 70 as shown in FIG. 7. Therefore, unlike the prior-art method wherein light interception is effected by the operation of mechanically inserting and retracting the light intercepting member, no vibration occurs with the light intercepting operation. Accordingly, the optical system of the microscope is not subjected to vibration and the eye to be examined can be observed well through the optical system of the microscope.

Figure 10:
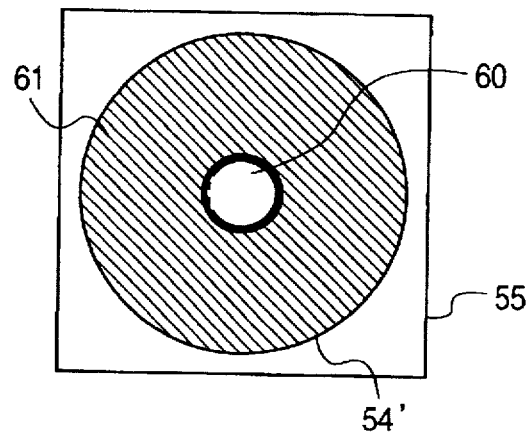
FIGS. 10 to 12 show other light intercepting states possible in the light intercepting member 55.
Figure 11:
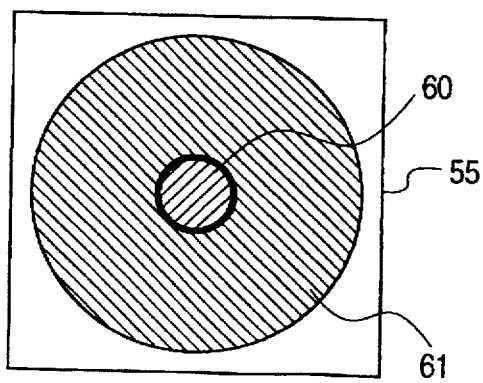
Figure 12:
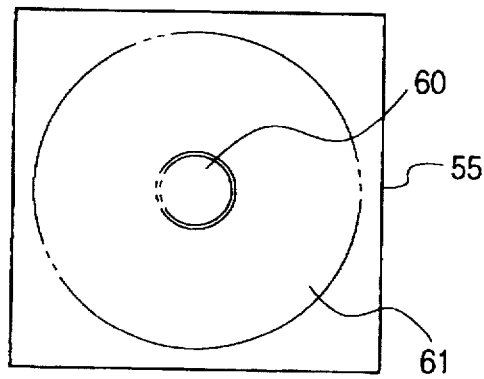

FIGS. 10 to 12 show other light intercepting states possible in the light intercepting member 55.

In the light intercepting state shown in FIG. 10, the central light intercepting portion 60 transmits the illuminating light therethrough and the marginal light intercepting portion 61 intercepts the illuminating light with a predetermined transmission factor. In this light intercepting state, only the pupil part of the eye 59 to be examined is illuminated brightly. Accordingly, the retro-illuminated image can be observed with good contrast without getting mixed with marginal light and the minute observation of the crystalline lens part can be accomplished, and this is useful in case of the removal or the like of the crystalline lens.

Also, in the light intercepting state shown in FIG. 11, both of the central light intercepting portion 60 and the marginal light intercepting portion 61 intercept the illuminating light with a predetermined transmission factor. In this light intercepting state, the whole of the light intercepting portion 56 has an effect equal to that of a density filter, and a momentary increase in the illuminating light to the pupil of the eye 59 to be examined and the portion around it is possible.

Further, in FIG. 12, both of the central light intercepting portion 60 and the marginal light intercepting portion 61 transmit the illuminating light therethrough. In this case, there can be formed the same state as the ordinary illuminating state in which the light intercepting member 55 is not inserted.

Figure 13:
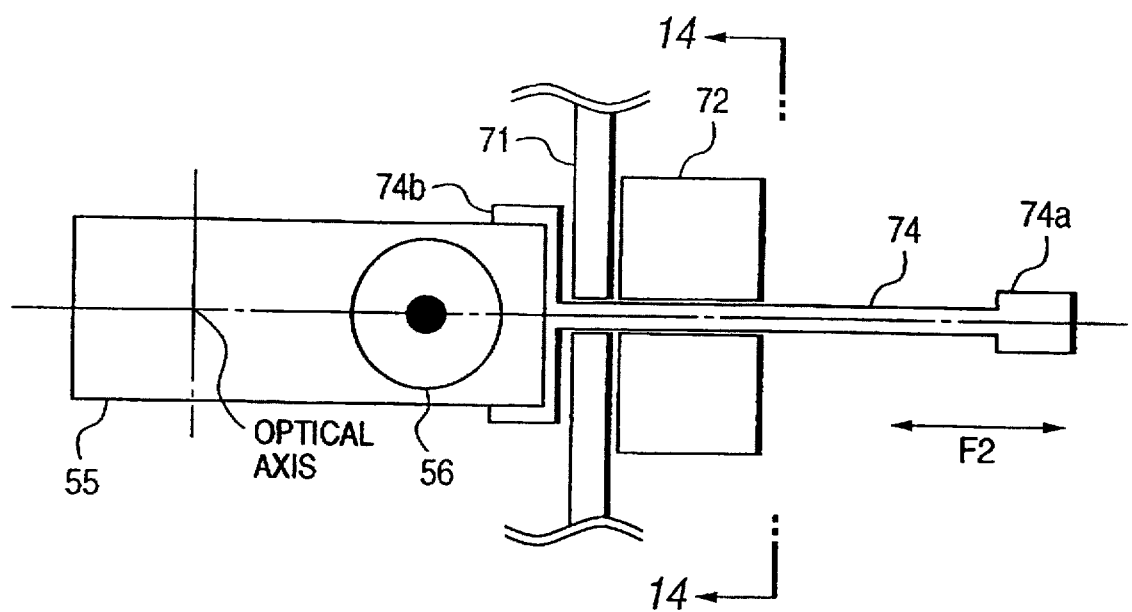
FIG. 13 is a cross-sectional view of a mechanism for selecting a desired light intercepting state.
Figure 14:
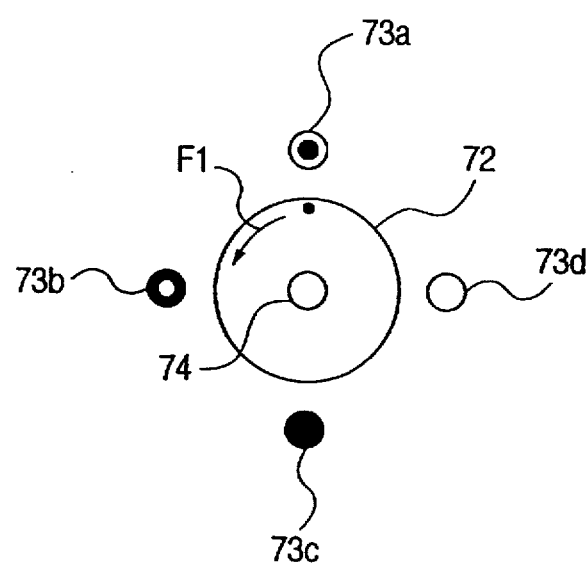
FIG. 14 is a view along the line 14—14 of FIG. 13.

FIGS. 13 and 14 schematically show the construction of a mechanism for selecting a desired light intercepting state, FIG. 13 being a cross-sectional view, and FIG. 14 being a view taken along the line 14—14 of FIG. 13.

As described above, in the second embodiment, the voltage applied to the electrical light control element constituting the central light intercepting portion 60 and the voltage applied to the electrical light control element constituting the marginal light intercepting portion 61 are controlled through the control system 70, whereby there can be realized the four typical light intercepting states as shown in FIGS. 9 to 12.

It is desirable that the selecting mechanism for the light intercepting states be provided in any other portion than the microscope body so as not to give harmful vibration to the microscope. However, when the selecting mechanism must be installed in the microscope body, it is desirable from the viewpoints of the operability and the downsizing of the mechanism to use a single changeover switch.

So, in the selecting mechanism of FIGS. 13 and 14, a changeover switch 72 is rotated in the direction of arrow F1 to thereby select marks 73a to 73d formed on the housing portion 71 of the microscope body. The marks 73a to 73d correspond to the light intercepting states of FIGS. 9 to 12, respectively. Thus, a mark corresponding to a desired light intercepting state is selected by the changeover switch 72, whereby the desired light intercepting state can be realized in the light intercepting member 55.

Also, the selecting mechanism of FIG. 14 is provided with a rod 74 for driving the light intercepting portion 56 of the light intercepting member 55 forward and backward relative to the illuminating optical path. The rod 74 extends through the changeover switch 72 and the housing portion 71, and has a knob portion 74a formed on one end thereof, and has a grip portion 74b for gripping the light intercepting member 55 formed on the other end thereof.

Thus, the rod 74 is suitably driven in the direction of arrow F2, whereby the light intercepting portion 56 of the light intercepting member 55 can be inserted into or retracted from the illuminating optical path at any time.

Figure 15:
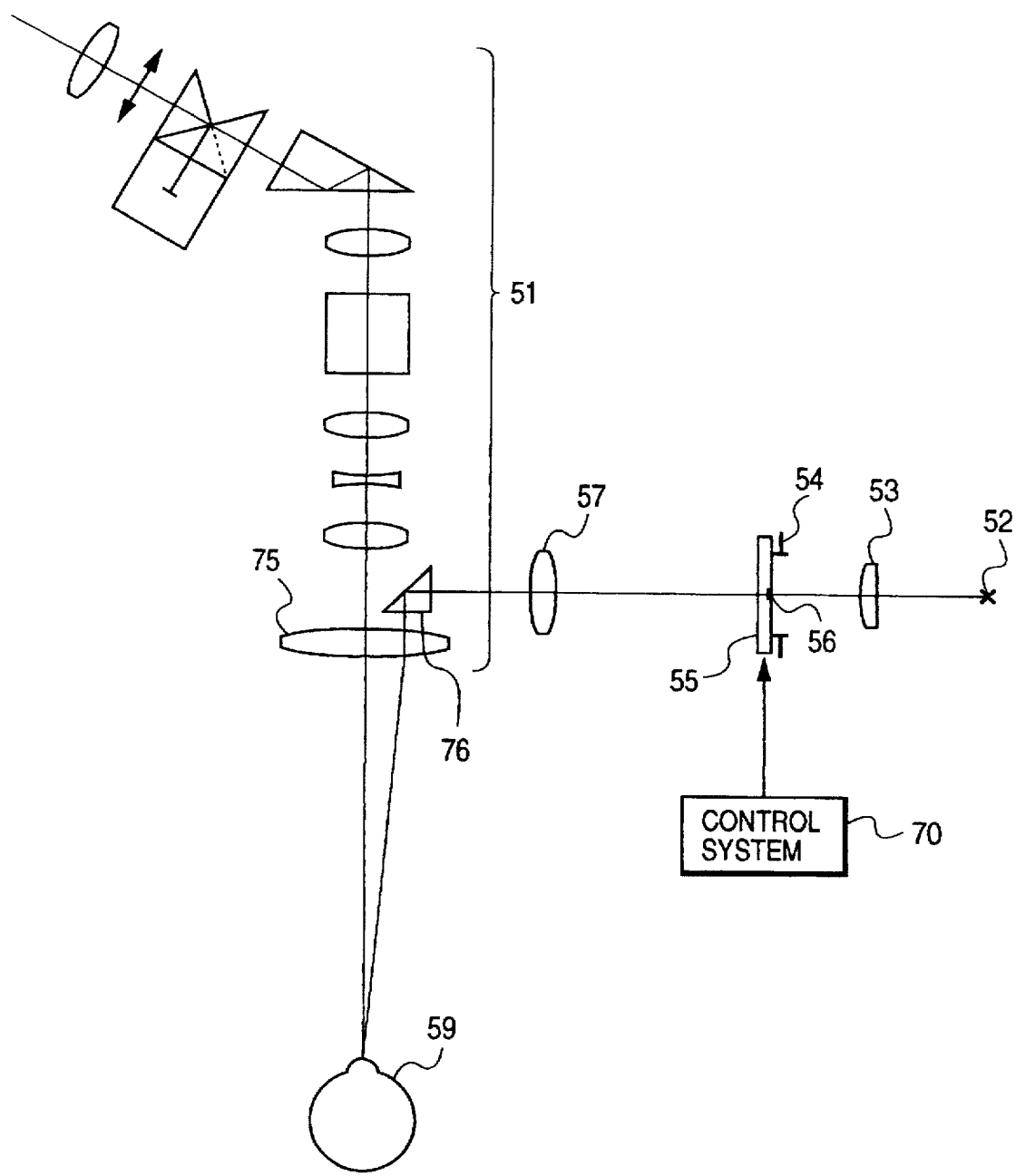
FIG. 15 shows an example of the construction of an optical system according to a third embodiment.

FIG. 15 shows the construction of an ophthalmic illumination device according to a third embodiment of the present invention together with the optical system of a microscope. The device according to the third embodiment has a construction similar to that of the device according to the second embodiment, but basically differs only in that a prism 76 is introduced instead of the light dividing means 58 in the second embodiment and the illuminating light deflected by the prism 76 is caused to enter the eye to be examined through the objective lens 75 of the optical system 51 of the microscope.

The other constructions and operations of the third embodiment are similar to those of the second embodiment and need not be described.

As the electrical light control element, it is desirable from the viewpoints of the magnitude of a variation in transmission factor and the simplicity of the handling thereof to use an electrochromic element of the whole solid type.

Also, with regard to the injury with light of the fundus part of the eye to be examined, it is pointed out that light of short wavelength is more dangerous than light of long wavelength. Accordingly, it is desirable that the light intercepting portion be an electrical light control element of such structure that reduces the transmission factor of the light of shorter wavelength.

Figure 16:
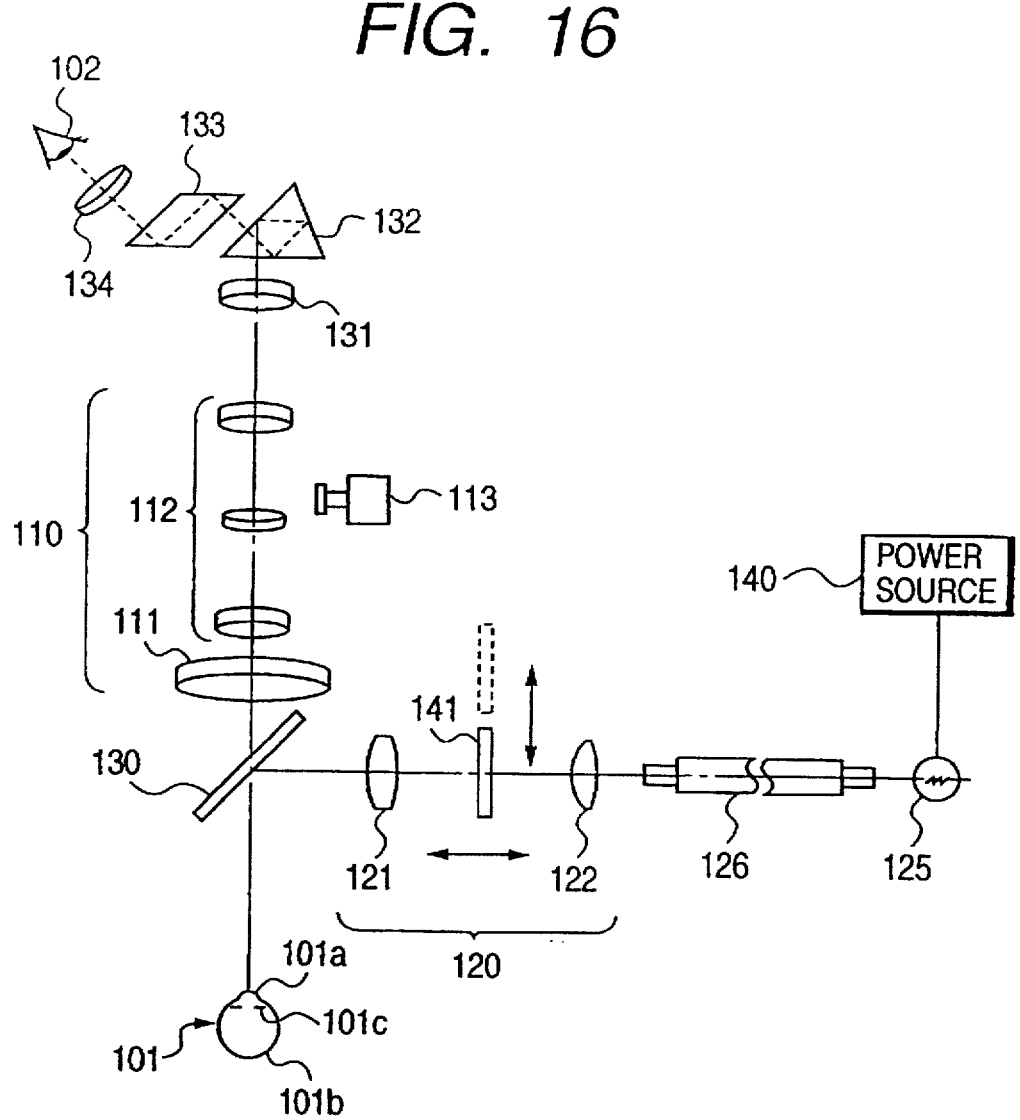
FIG. 16 is an optical path view showing an example of the construction of an optical system according to a fourth embodiment.

FIG. 16 shows the optical system of a microscope for operation to which an ophthalmic illumination device according to a fourth embodiment of the present invention is applied.

As shown in FIG. 16, as an optical construction for observing an eye 101 to be operated, provision is made of a first objective lens 111, a pair of right and left variable magnification optical systems (only one optical path being shown) 112, a zoom potentiometer 113 for detecting the zoom magnification in the variable magnification optical systems 112, and a pair of imaging optical systems provided correspondingly to the respective variable magnification optical systems 112 for forming the observation image of the eye 101 to be operated on an operator's eye 102. Each of the imaging optical systems is comprised of a second objective lens 131, an erect prism 132, a lozenge-shaped prism 133 and an eyepiece 134.

The microscope for operation is further provided, as an optical construction for illuminating the eye 101 to be operated, with an illuminating light source 125, an illumination power source 140 for controlling the supply of electric power to the light source 125, an optical fiber 126 for directing the illuminating light from the light source 125 to an illuminating optical system 120, and a half mirror 130 for deflecting the illuminating light from the illuminating optical system 120 toward the eye 101 to be operated.

In the present embodiment, the illuminating optical system 120 is provided with a condenser lens 122 and a relay lens 121 for condensing the illuminating light from the optical fiber 126 and directing it to the half mirror 130, a pattern display member 141 of the light transmitting type disposed between the two lenses 121 and 122 and forming a fixation target (pattern) to be recognized by the eye 101 to be examined, and a display member driving portion 142 (see FIG. 23) for electrically driving the pattern display member 141 to thereby cause a predetermined pattern to be displayed.

As the pattern display member 141 of the light transmitting type, use is made, for example, of a pattern display member (hereinafter called the liquid crystal filter) comprised of a liquid crystal device and capable of forming any pattern, or a pattern display member (hereinafter called the ECD filter) comprised of an electrochromic device (ECD) and capable of selectively displaying one or more preset patterns.

Of course, in the present invention, the pattern display member 141 may be any other one capable of displaying such patterns as exemplarily shown below than the above described liquid crystal filter or ECD filter.

The pattern display member 141 is supported by a slide bearing so as to be movable in the direction of the optical axis of the illuminating optical system 120 so that it can be disposed at a position conjugate with the retina 101b of the eye 101 to be examined so that a pattern displayed can be recognized by the eye 101 to be examined, and further can be disposed at positions conjugate with the cornea 101a and iris 101c of the eye 101 to be examined, and at the in-focus position of the microscope for operation.

Further, the pattern display member 141 is installed for displacement in a direction orthogonal to the direction of the optical axis of the illuminating optical system 120 so that when the presentation of a pattern is unnecessary, the pattern display member 141 can be retracted out of the optical path of the illuminating optical system 120.

Design may be made such that the movement of the pattern display member 141 in the direction of the optical axis and in the direction orthogonal thereto is directly effected by a manual operation or effected by the use of an actuator and control means therefor.

In the present embodiment, the observation image of the eye 101 to be examined passes through the half mirror 130, the first objective lens 111 and the pair of right and left variable magnification optical systems 112. The image of the eye to be examined having passed through the variable magnification optical systems 112 passes through the second objective lens 131, the erect prism 132 and the lozenge-shaped prism 133, and is formed on the operator's eye 102 by the eyepiece 134. On the other hand, the illumination to the eye 101 to be examined passes from the light source 125 through the optical fiber 126 and through the illuminating optical system 120 comprising the condenser lens 122 and the relay lens 121, and is deflected toward the eye 101 to be examined by the half mirror 130.

In the illuminating optical system 120, the pattern display member 141 comprised of an ECD filter, a liquid crystal filter or the like is disposed for movement in the direction of the optical axis and in a direction orthogonal thereto.

Patterns displayed by the pattern display member 141 in the present embodiment will now be described with reference to FIGS. 17 to 22.

Figure 17:
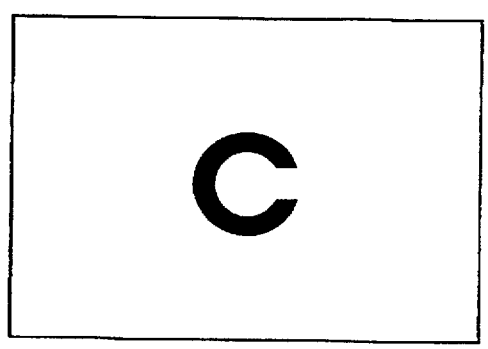
FIGS. 17 to 22 show examples of a pattern formed in the fourth embodiment.
Figure 18:
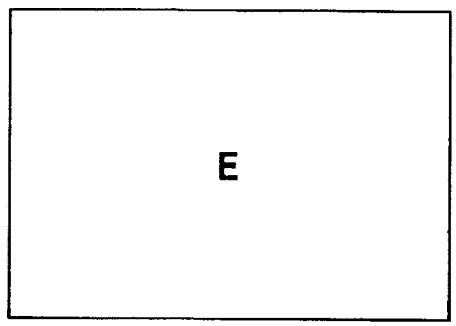

When the microscope for operation according to the present invention is to be used, for example, in an operation on cataract, when an IOL (intraocular lens) is inserted into the eye and thereafter a subjective test is performed to determine a degree of sight level, a sight chart as shown in FIG. 17 or 18 is displayed as a pattern. In this case, the pattern display member 141 is disposed at a location in the illuminating optical system 120 which is conjugate with the retina 101b of the eye 101 to be examined. It is to be understood here that the pattern display member 141 can display a plurality of kinds of sight charts as described above while changing the sizes thereof. This pattern display member 141 is controlled to display one of the sight charts as described above and project it onto the retina 101b of the eye 101 to be examined, whereby it becomes possible to know the sight level after the insertion of the IOL.

The above-described sight testing method is of course useful also in RK (radial keratotomy) operation and PRK (photo refractive keratotomy) operation.

Figure 19:
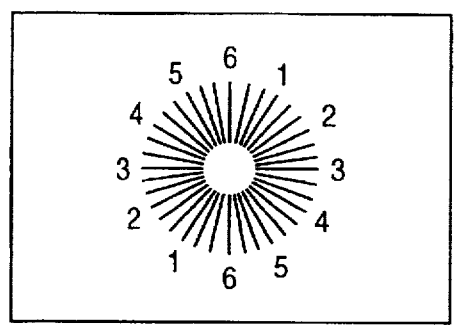

Also, during AK (astigmatism keratotomy) operation for correcting astigmatism which may occur in an ophthalmic operation such as above-described operation on cataract, RK operation or PRK operation or congenital astigmatism, for example, an astigmatism chart as shown in FIG. 19 is displayed. Such an astigmatism chart is projected onto the retina 101b of the eye 101 to be examined, whereby it becomes possible to carry out an operation while confirming the condition of correction of astigmatism with the patient.

Figure 20:
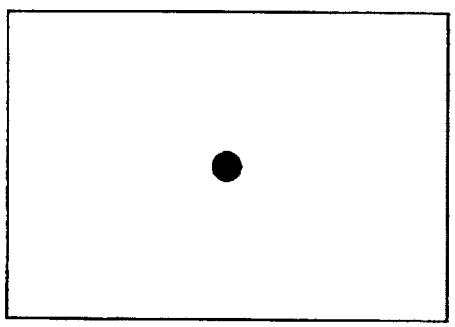

Also, to make the eye 101 to be examined fixate, a pattern of black point as shown, for example, in FIG. 20 is used as an eye fixation target. Again in this case, the pattern display member 141 is disposed at a location in the illuminating optical system 120 which is conjugate with the retina 101b of the eye 101 to be examined. By changing the displayed position of the black point pattern on the display surface of the pattern display member 141 in XY direction, it becomes possible for the operator to turn the eye 101 to be examined to a direction desired by the operator.

Figure 21:
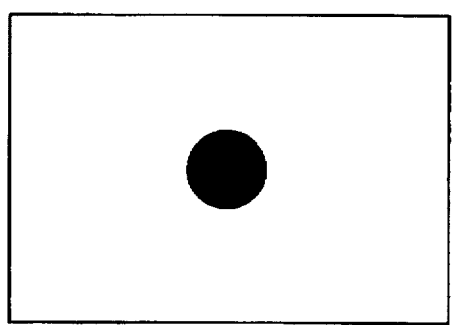

Also, when the retina 101b of the eye 101 to be examined is to be protected from the illuminating light or the like, a pattern of black point as shown, for example, in FIG. 21 is displayed. In this case, the pattern display member 141 is disposed at a location in the illuminating optical system 120 which is conjugate with the iris 101c or the cornea 101a of the eye 101 to be examined.

By adjusting the displayed position of this black point pattern on the display surface of the pattern display member 141, it is possible to cover the retina 101b of the eye 101 to be examined even if the position of the pupil of the eye 101 to be examined is not at the center of the field of view of the microscope for operation. Further, by changing the displayed size of the black point pattern on the display surface of the pattern display member 141, it becomes possible to adjust the size of the black point to the size of the pupil of the eye 101 to be examined.

Figure 22:
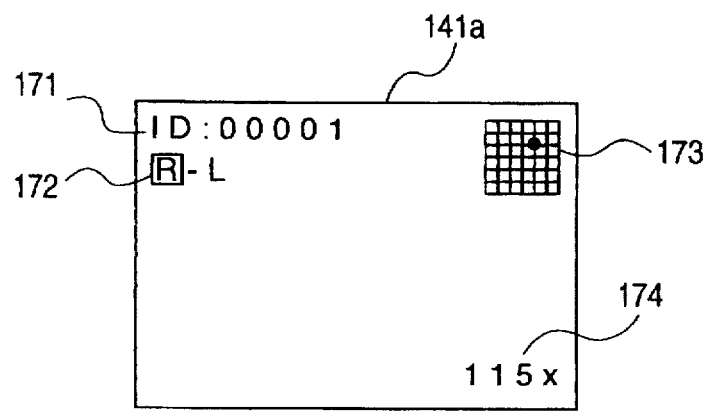

Also, when it is desired to know various kinds of information about the patient, the operated state of the microscope for operation, etc., a pattern as shown, for example, in FIG. 22 which indicates the various kinds of information at respective locations is projected onto the cornea 101a of the eye 101 to be examined simply or together with the patterns as shown in FIGS. 17 to 21, and the operator looks at it through the microscope. This pattern includes, for example, the patient's ID number 171, information 172 for distinguishing whether the eye being operated is the right eye or the left eye, information 173 indicative of the position of the microscope for operation relative to the affected part, the magnification information 174 of the microscope for operation, etc. In this case, the pattern display member 141 is disposed at a location in the illuminating optical system 120 which is conjugate with the cornea 101a of the eye 101 to be examined.

Figure 23:
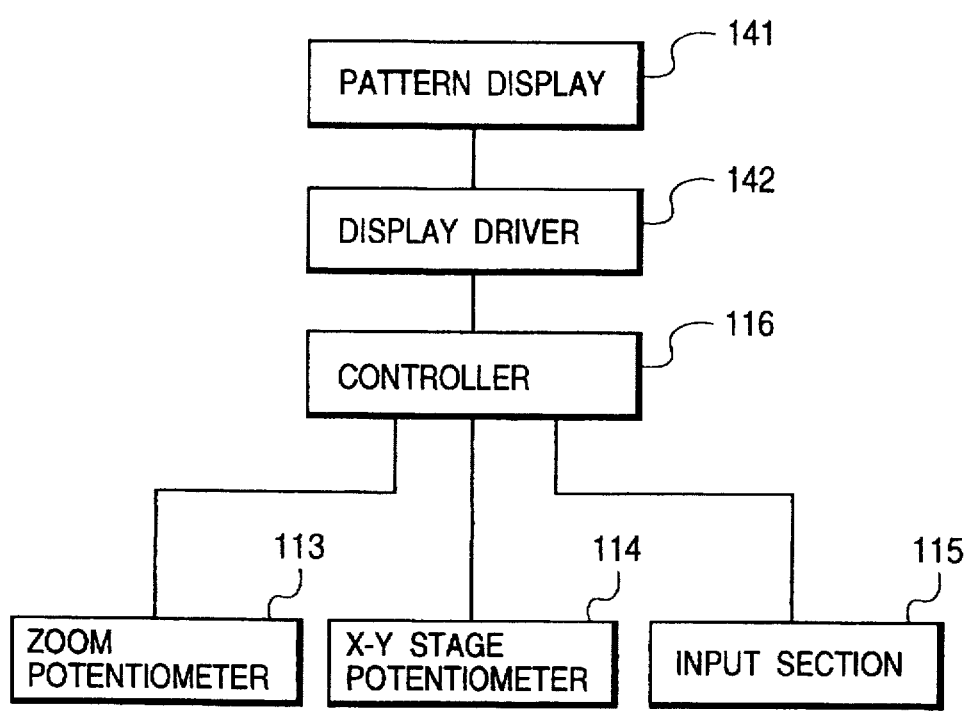
FIG. 23 is a block diagram showing an example of the construction of an electric control system in the fourth embodiment.
Figure 24:
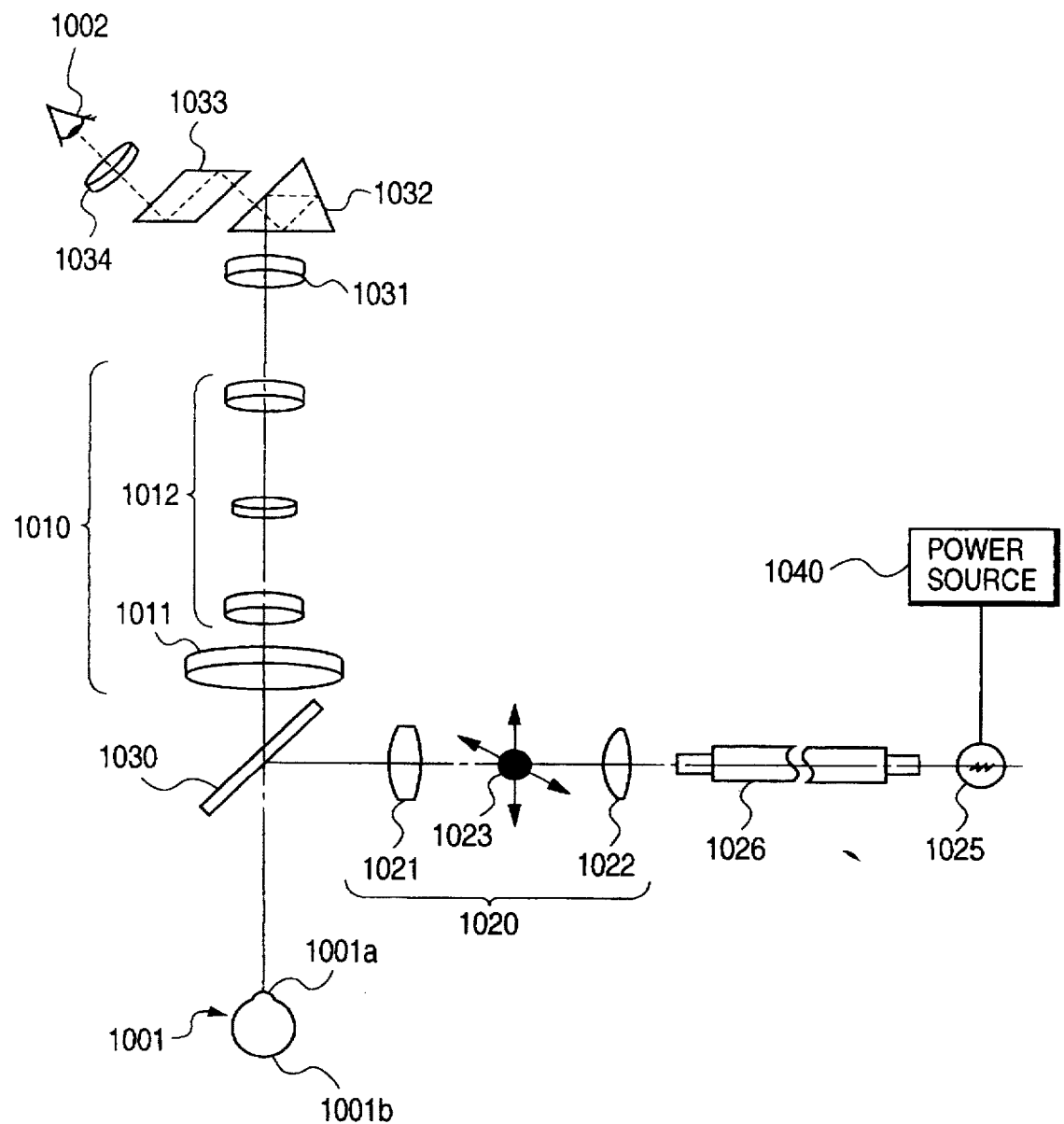
FIG. 24 is an illustration showing the optical arrangement in a microscope for operation according to the prior art.
Figure 25:
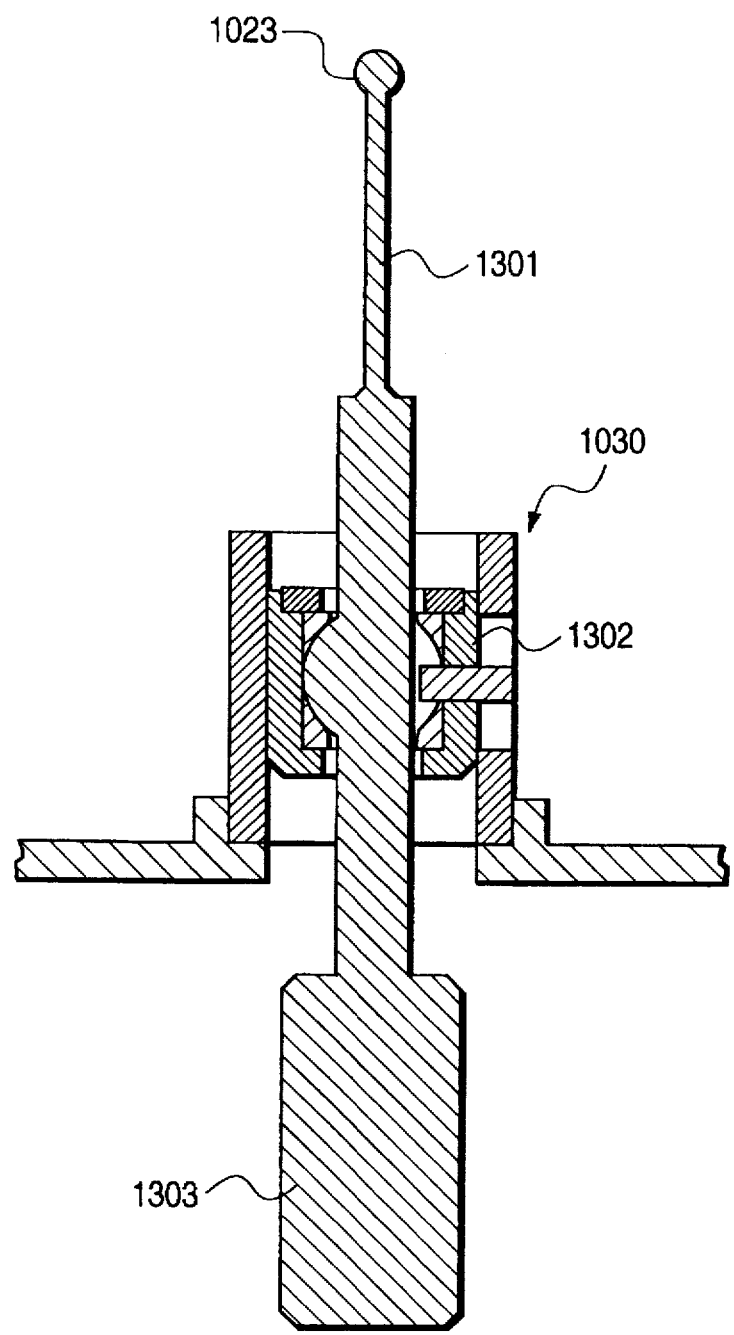
FIG. 25 is a cross-sectional view showing the construction of an eye fixation target moving mechanism in the microscope for operation according to the prior art.

In the present embodiment, a circuit construction as shown, for example, in FIG. 23 is used when the pattern of FIG. 22 is to be displayed. This circuit construction is provided with a controller 116 for controlling a display driver 142 for driving the pattern display member 141 to thereby cause each kind of inputted information to be displayed on a predetermined area on the display surface of the pattern display member 141. This circuit construction is further provided with a zoom potentiometer 113 connected to the controller 116 and outputting magnification information for inputting the information to be displayed, an X-Y stage potentiometer 114 outputting the positional information of the X-Y stage, and an input section 115 for receiving an input operation regarding the information about the patient's ID number and the destination between the right and left eyes and outputting information corresponding to each received operation.

According to the present embodiment, as described above, it becomes possible for the operator to present a predetermined pattern at a position conjugate with the retina 101b of the eye 101 to be examined to the eye 101 to be examined during an operation to thereby carry out various tests of sight, astigmatism, the field of view, etc. easily.

Further, according to the present embodiment, it becomes possible to move the displayed position of a pattern from a position conjugate with the retina 101b of the eye 101 to be examined, and dispose the pattern, for example, at a position conjugate with the pupil position (iris position) 101a of the eye 101 to be examined and use it as a filter for retina protection, or to move the displayed position of the pattern to a position conjugate with the in-focus position of the microscope for operation, and project various kinds of information such as the ID information of the eye 101 to be examined, the microscope magnification information and the positional information of the X-Y stage.

Further, according to the present embodiment, when any pattern is not necessary, it becomes possible to control the device so as not to display the pattern, or to retract the pattern display member 141 out of the optical path.

What is claimed is:

1. An ophthalmic illumination device comprising:
   an illuminating optical system for illuminating an eye to be examined;
   a light transmitting member disposed in the optical path of said illuminating optical system and having a light transmitting surface variable in the transmission factor for illuminating light; and
   a control unit for varying the transmission factor of a predetermined area of the light transmitting surface of said light transmitting member.

2. The ophthalmic illumination device of claim 1, wherein said light transmitting member is a liquid crystal device of the transmission type.

3. The ophthalmic illumination device of claim 2, wherein when said eye to be examined is illuminated, said control unit varies the transmission factor of a predetermined area of said liquid crystal device to thereby form at a predetermined position on said liquid crystal device a black point for protecting the retina of said eye to be examined from the illuminating light.

4. The ophthalmic illumination device of claim 3, further comprising:
   an observation optical system for observing the eye to be examined;
   an image pickup device for receiving image of the eye to be examined directed from the field of view of said observation optical system; and
   an image processing device for calculating the position of a particular region of said image of the eye to be examined in said field of view based on said image of the eye to be examined introduced by said image pickup device; and
   wherein said control unit forms said black point at the position of the particular region of said image of the eye to be examined calculated by said image processing device.

5. The ophthalmic illumination device of claim 3, further comprising:
   a driving mechanism for moving a microscope body relative to said eye to be examined; and
   a movement amount detecting device for detecting the amount of movement of said microscope body;
   wherein said control unit changes the position of said black point in accordance with the amount of movement detected by said movement amount detecting device.

6. The ophthalmic illumination device of claim 1, wherein said light transmitting member has a circular central area corresponding to the pupil of said eye to be examined, and a marginal area surrounding said central area, and said control unit varies the light transmission factor of said central area and said marginal area independently of each other.

7. The ophthalmic illumination device of claim 6, wherein said light transmitting member is provided at a position optically conjugate with the pupil of said eye to be examined.

8. The ophthalmic illumination device of claim 6, wherein said control unit is provided with a selector for selecting one of a first light intercepting state in which the transmission factor of said central area is smaller than the transmission factor of said marginal area, a second light intercepting state in which the transmission factor of said central area is greater than the transmission factor of said marginal area, a third light intercepting state in which both of the transmission factor of said central area and the transmission factor of said marginal area are small, and a fourth light intercepting state in which both of the transmission factor of said central area and the transmission factor of said marginal area are great.

9. The ophthalmic illumination device of claim 6, wherein said light transmitting member is an electrochromic element of the whole solid type.

10. The ophthalmic illumination device of claim 1, wherein said light transmitting member is provided at a position optically conjugate with the retina part of said eye to be examined, and said control unit varies the transmission factor of a predetermined area of the light transmitting surface of said light transmitting member to thereby form a fixation target to be recognized by an examinee.

11. The ophthalmic illumination device of claim 10, wherein said control unit forms either a sight chart or a black point to be fixated at by said eye to be examined as said fixation target.

12. The ophthalmic illumination device of claim 10, wherein said light transmitting member is provided for movement in the direction of the optical axis of said illuminating optical system, and the range of movement thereof covers positions optically conjugate with the cornea part and fundus part of said eye to be examined.

13. The ophthalmic illumination device of claim 10, wherein said light transmitting member is insertable into and retractable from the optical path of said illuminating optical system.

14. A microscope for operation comprising:
- an illuminating optical system for illuminating an eye to be examined;
- an observation optical system for observing therethrough the eye to be examined illuminated by said illuminating optical system;
- a light transmitting member disposed in the optical path of said illuminating optical system and having a light transmitting surface variable in the transmission factor for illuminating light; and
- a control unit for varying the transmission factor of a predetermined area of the light transmitting surface of said light transmitting member.

15. The microscope for operation of claim 14, wherein said light transmitting member has a circular central area corresponding to the pupil of said eye to be examined, and a marginal area surrounding said central area, and said control unit varies the light transmission factor of said central area and said marginal area independently of each other.

16. The microscope for operation of claim 14, wherein said light transmitting member is provided at a position optically conjugate with the retina part of said eye to be examined, and said control unit varies the transmission factor of a predetermined area of the light transmitting surface of said light transmitting member to thereby form a fixation target to be recognized by an examinee.

* * * * *